US010729191B2

(12) United States Patent
DeLise (10) Patent No.: US 10,729,191 B2
(45) Date of Patent: Aug. 4, 2020

(54) MEDICAL SUPPORT DEVICE

(71) Applicant: Joseph DeLise, Maplewood, NJ (US)

(72) Inventor: Joseph DeLise, Maplewood, NJ (US)

(*) Notice: Subject to any disclaimer, the term of this patent is extended or adjusted under 35 U.S.C. 154(b) by 410 days.

(21) Appl. No.: 15/857,851

(22) Filed: Dec. 29, 2017

(65) Prior Publication Data

US 2019/0200691 A1  Jul. 4, 2019

(51) Int. Cl.
| | | |
|---|---|---|
| *A41D 13/12* | (2006.01) | |
| *A61F 15/00* | (2006.01) | |
| *A61F 13/00* | (2006.01) | |
| *A61F 13/84* | (2006.01) | |

(52) U.S. Cl.
CPC .... *A41D 13/1236* (2013.01); *A61F 13/00051* (2013.01); *A61F 15/008* (2013.01); *A61F 2013/8479* (2013.01)

(58) Field of Classification Search
CPC ..... A47C 21/024; A47C 21/00; A47C 15/008; A47C 27/00; A61G 7/053; A61G 7/1026; A61G 7/1049; A61F 2013/8479; A61F 15/008; A61F 13/00051; B60L 13/04; H02N 15/00; A47G 9/02; A47G 2009/002; A41D 13/0007; A61H 1/00; H01F 7/02; A61N 2/00
USPC .... 128/888, 889, 869–884; 5/503, 421, 490, 5/693; 602/14
See application file for complete search history.

(56) References Cited

U.S. PATENT DOCUMENTS

| | | | | |
|---|---|---|---|---|
| 5,172,436 A | * | 12/1992 | Masuda | A47C 27/144 5/690 |
| 5,667,461 A | * | 9/1997 | Hall | A61H 1/0229 472/15 |
| 6,626,820 B1 | * | 9/2003 | Ardizzone | A47J 47/16 5/693 |
| 8,174,347 B2 | * | 5/2012 | Fullerton | E05C 19/16 335/285 |

(Continued)

FOREIGN PATENT DOCUMENTS

KR   20090023749 A  *  3/2009

OTHER PUBLICATIONS

EPO Translation of Lee, KR-20090023749-A (Year: 2009).*

*Primary Examiner* — Alireza Nia
*Assistant Examiner* — Samuel B. Lum
(74) *Attorney, Agent, or Firm* — John Laurence (57) ABSTRACT

A medical surgical wound support device comprising a flexible support garment designed to be worn by a patient, the flexible support garment having an inner surface that comes in direct contact with the patient and an outer surface facing outward from the patient, a plurality of permanent magnets embedded within the flexible support garment, each of which is oriented such that its north magnetic pole faces the outer surface, a rigid base component, that has an outer surface facing upward from a support on which the rigid support structure rests, a plurality of permanent magnets embedded within the outer surface of the rigid base component, each embedded magnet oriented such that the north magnetic pole faces the outer surface; and a repelling magnetic force originating from the outer surface of the flexible support garment and the outer surface of the rigid base component such that a portion of the patient wearing the flexible support garment is elevated a controllable distance above the rigid base component.

7 Claims, 9 Drawing Sheets

(56) References Cited

U.S. PATENT DOCUMENTS

| | | | | |
|---|---|---|---|---|
| 2006/0065274 A1* | 3/2006 | Mathis | ............... | A61B 46/23 |
| | | | | 128/849 |
| 2010/0256772 A1* | 10/2010 | Skerven | ............... | A61F 2/94 |
| | | | | 623/23.7 |
| 2012/0317713 A1* | 12/2012 | Eytan | ............... | A61G 7/1026 |
| | | | | 5/81.1 R |
| 2018/0303689 A1* | 10/2018 | Souke | ............... | A61G 1/0567 |
| 2019/0142670 A1* | 5/2019 | Nomura | ............... | A61G 5/10 |
| | | | | 5/86.1 |

* cited by examiner

MEDICAL SUPPORT DEVICE

BACKGROUND

A great deal of pain associated with post-surgical wound is the result of pressure from a person's own weight or tight garments and surgical dressings being applied to that wound. There is currently no known method provided to elevate a wound to the point of actual pain reduction. One way to help alleviate pressure on a wound and the resulting pain is to use magnets to levitate the area surrounding the wound while remaining clear of the wound itself and thereby remove any pressure. This solution also helps eliminating the need for a patient to remain lying in a position that is either uncomfortable, limits mobility or creates additional issues to help alleviate the pain. At times, the use of pillows, mechanical attachments, overstuffed comforters or padded chairs have been used in an attempt to reduce pain associated with a wound. A patient has even more of a challenge for pain reduction in an in home or even an automotive/transportation situation.

SUMMARY

In an effort to address the above described problems, the present invention discloses a magnetic levitation device that aids in the healing of a patient's wound. Specifically, the present invention discloses a medical surgical wound support device comprised of a flexible support garment designed to be worn by a patient, the flexible support garment having a inner surface come in direct contact with the patient and an outer surface facing outward from the patient, a plurality of permanent magnets embedded within the flexible support garment, each embedded magnet oriented such that its north magnetic pole faces the outer surface, a rigid base component, the rigid base component having an outer surface facing upward from a support on which the rigid support structure rests, a plurality of permanent magnets embedded within the outer surface of the rigid base component, each embedded magnet oriented such that the north magnetic pole faces the outer surface, and a repulsive magnetic force originating from the outer surface of the flexible support garment and the outer surface of the rigid base component such that a portion of the patient wearing the flexible support garment is elevated a controllable distance above the rigid base component.

DETAILED DESCRIPTION OF THE INVENTION

Figure 1A:
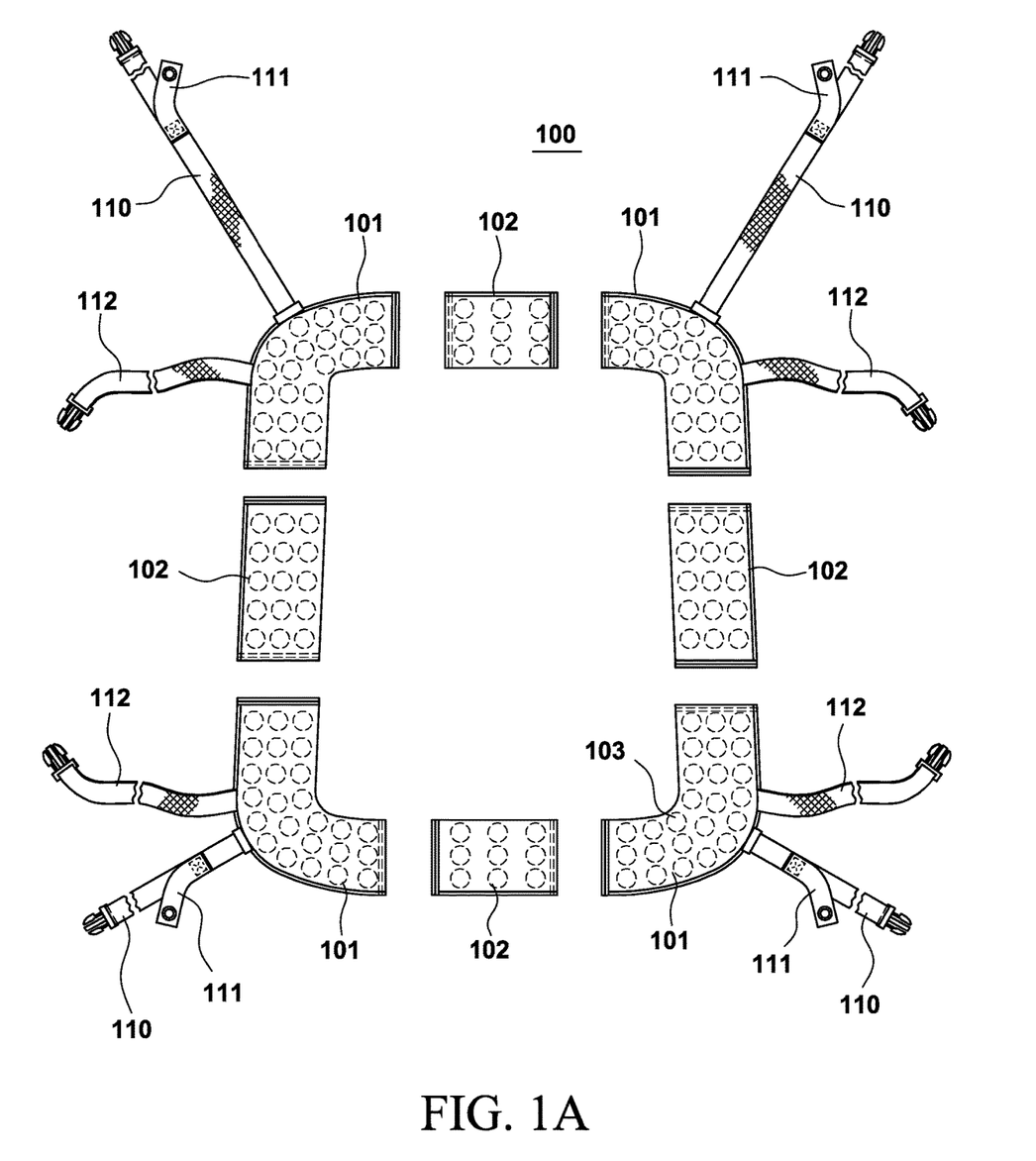
FIGS. 1A and 1B are a flexible support garment with embedded magnets showing its components separated and connected, respectively, according to an exemplary embodiment.
Figure 1B:
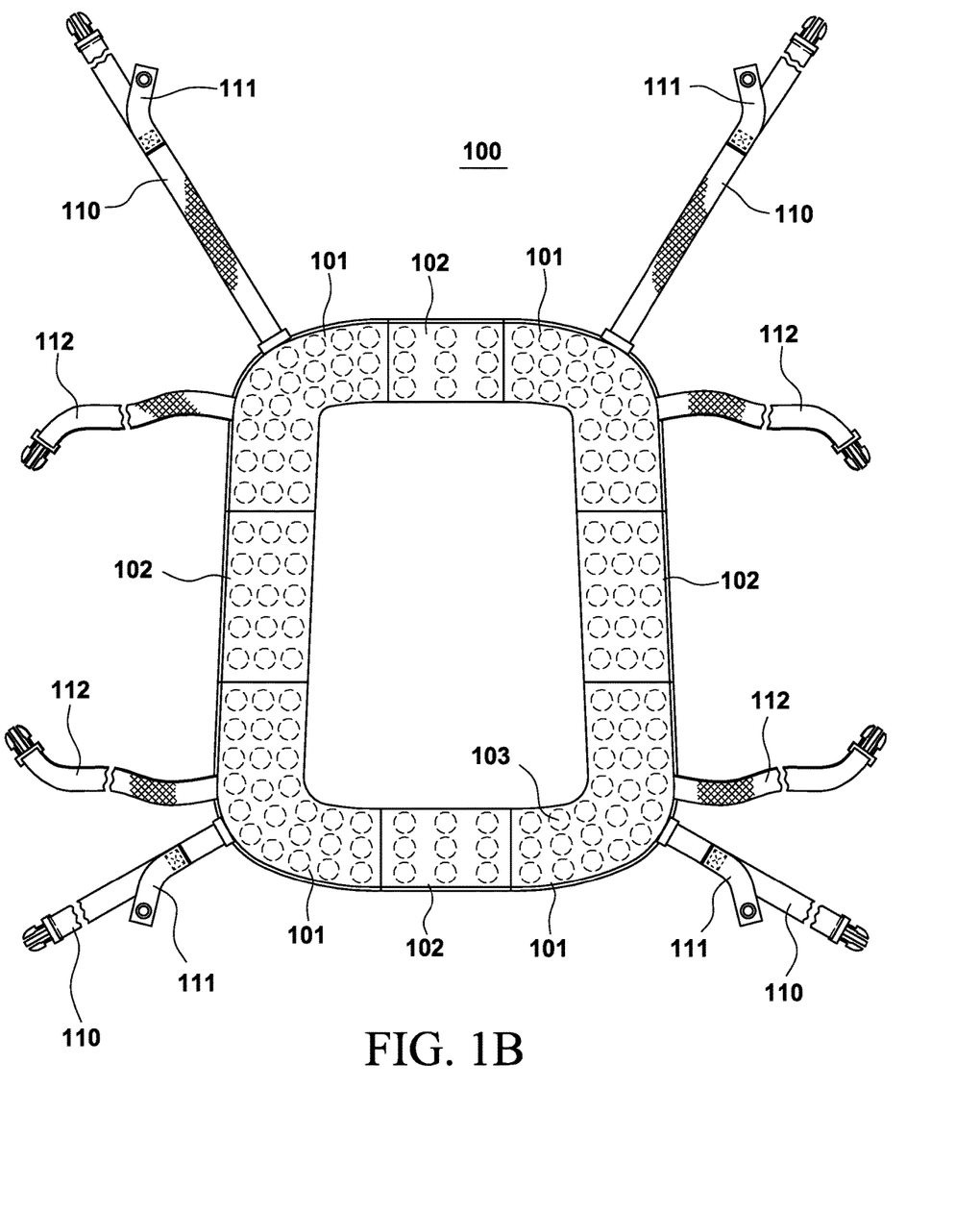

In FIGS. 1A and 1B, a flexible support garment with embedded magnets showing its components separated and connected, respectively, according to an exemplary embodiment are shown. As shown in FIGS. 1A and 1B, the flexible support garment 100 is comprised of at least four interconnecting corner components 101 and possibly one or more size expansion components 102 positioned in-between and interconnecting with any two corner components 101. The inclusion and positioning of one or more size expansion components 102 in-between any two corner components 101 allows for variations in size and shape of the resulting flexible support garment 100 as to satisfy the needs of a patient wearing the flexible support garment 100. As further shown in FIG. 1, the corner components 101 and the size expansion components 102 each include a plurality of embedded permanent magnets 103.

Figure 2:
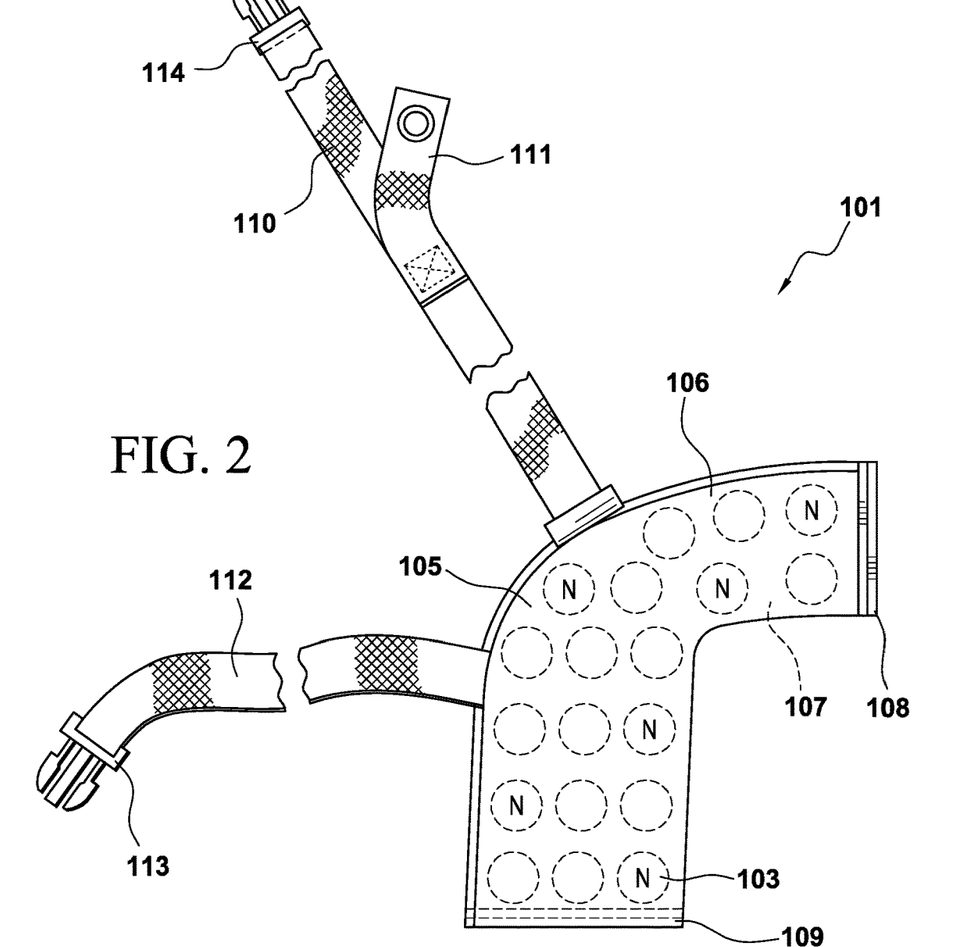
FIG. 2 is a corner component of the flexible support garment with embedded magnets according to the exemplary embodiment.

In FIG. 2, a corner component of the flexible support garment with embedded magnets according to the exemplary embodiment is shown. As shown in FIG. 2, the corner component 101 includes an L shaped body member 105 made of an elastic and flexible non-metallic fabric. The L shaped body member 105 includes an inner surface 107 that comes in direct contact with a portion of a patient's back and an outer surface 106 that faces outward from the patient's back.

A plurality of permanent magnets 103 are embedded and secured within the elastic and flexible non-magnetic fabric comprising the body member 105. The plurality permanent magnets 103 are spaced evenly apart and are oriented such that each magnet's magnetic north pole N radiated outward from the outer surface 106. The elastic and flexible non-magnetic fabric comprising the body member 105 is non-ferrous as to not interfere with the magnetic fields emanating from the evenly distributed and similarly oriented embedded permanent magnets 103.

While the disclosed embodiments are not limited to any particular type of permanent magnets, an N52 grade neodymium magnet is been found to be minimally suitable for the required purpose of the present invention. The plurality of permanent magnets 103 are evenly distributed and similarly oriented across the flexible support garment 100 as to provide a uniformly distributed magnetic field that interacts with a similar magnetic field emanating from a rigid base component, this interaction providing the required levitation of the flexible support garment 100.

Returning to FIG. 2, a male connector 108 is permanently attached to one end of the body member 105 and a corresponding female connector 109 is permanently attached to the other end of the body member 105. The connectors 108 and 109 are used to interconnect four corner components 100 alone or four corner components 100 with one or more size expansion components 102 to form a flexible support garment 100. The male and female connectors 108 and 109 have a dovetail and sleeve type configuration which minimizes its footprint across the surface area of the flexible garment 100 while maximizing flexibility.

A securing and rod locating strap 110 is permanently attached to the outer perimeter on the corner of the L shaped body member 105. The securing and rod locating strap 110 is designed to wrap around the torso or over the shoulders of the patient wearing the flexible support garment 100 and to interconnect with three other identical securing and rod locating straps 110 to secure the flexible support garment 100 onto the patient's back. Each securing and rod locating strap 110 includes a connector 114 that allows for adjustment of the length of each securing and rod locating strap 110 while securing the flexible support garment 100 to a specific patient.

A non-metallic rigid connection rod interface 111 is attached to each securing and rod locating strap 110, the position of the non-metallic rigid connection rod interface 111 being adjustable along the length of the securing and rod locating strap 110. As will be shown, the non-metallic rigid connection rod interface 111 couples to a rigid rod attached to a rigid base component, this coupling controlling the lateral and vertical movement of a patient wearing the flexile support garment 100 relative to that rigid base component.

A flexible connecting strap 112 is also permanently attached to the outer perimeter of the body member 105. A connector 113 on the flexible connecting strap 112 provides for adjusting the length of the flexible connecting strap 112, the connector 113 attaching to a complimentary connector on the rigid base component. The flexible connecting strap 112 functions to further limit the movement flexible support garment 100 relative to the rigid base component.

Figure 3:
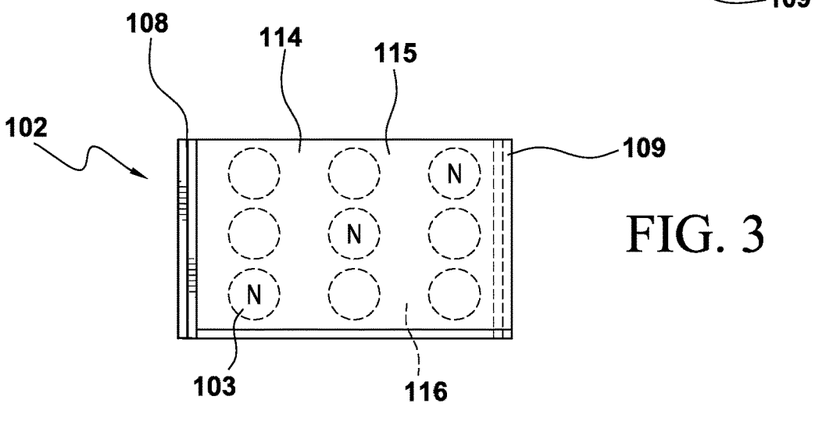
FIG. 3 is a size expansion component of the flexible support garment with embedded magnets according to the exemplary embodiment.

In FIG. 3, a size expansion component of the flexible support garment with embedded magnets according to the exemplary embodiment is shown. As shown in FIG. 3, the size expansion component 102 is composed of rectangular shaped body member 114 made of the same elastic and flexible non-ferrous fabric as the corner component 101. The body member 114 includes a inner surface 116 that comes in direct contact with the patient's back and an outer surface 115 that is outward facing from the patient's back.

As with the corner component 101, a plurality of permanent magnets 103 are embedded and secured within the elastic and flexible non-ferrous fabric comprising the body member 114. The permanent magnets 103 are evenly spaced apart and are oriented such that each magnet's magnetic north pole N emanates outward from the outer surface 115.

As also with the corner component 101, a male connector 108 is permanently attached to one end of the body member 114 and a corresponding female connector 109 is permanently attached to the other end of the body member 114. The male and female connectors 108 and 109 have these same dovetail and sleeve configuration and are designed to interact with the connectors on the corner component 101.

Figure 4:
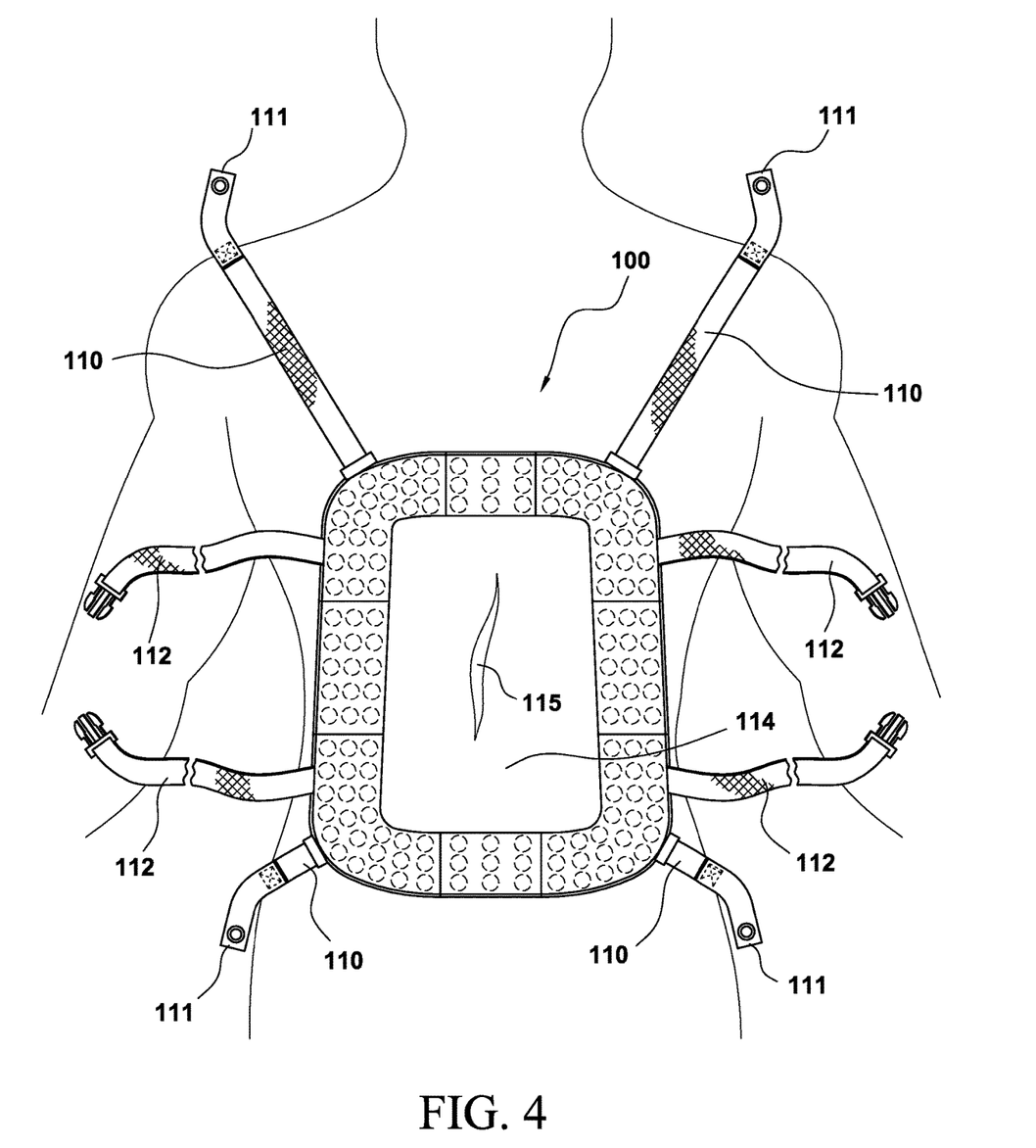
FIG. 4 is a rear posterior perspective view of a person wearing the flexible support garment with embedded magnets according to the exemplary embodiment.

In FIG. 4, a rear posterior perspective view of a person wearing the flexible support garment with embedded magnets according to the exemplary embodiment is shown. As shown in FIG. 4, the four corner components 101 are attached to each other and to one or more extension component 102 using the complementary connectors 108 and 109 to form a whole flexible support garment 100. The combination of components 101 and size expansion components 102 create a flexible support garment 100) whose custom shape includes an inner opening 114 that is specifically positioned to leave exposed a wound 115 on the patent's back. The corner components 101 may be combined with one or more size expansion components 102 to accommodate different patient sizes and wound locations.

As shown in FIG. 4, the securing and rod locating straps 110 are draped over the patient's shoulder and around the patient's waist and then secured across the patient's chest in a manner that secures the flexible support garment 100 onto the patient's back. The length of each securing and rod locating strap 110 may be adjusted to tighten or loosen the fit of the flexible garment 100 on the patient's back and accurately locate the vertical rods.

Figure 5:
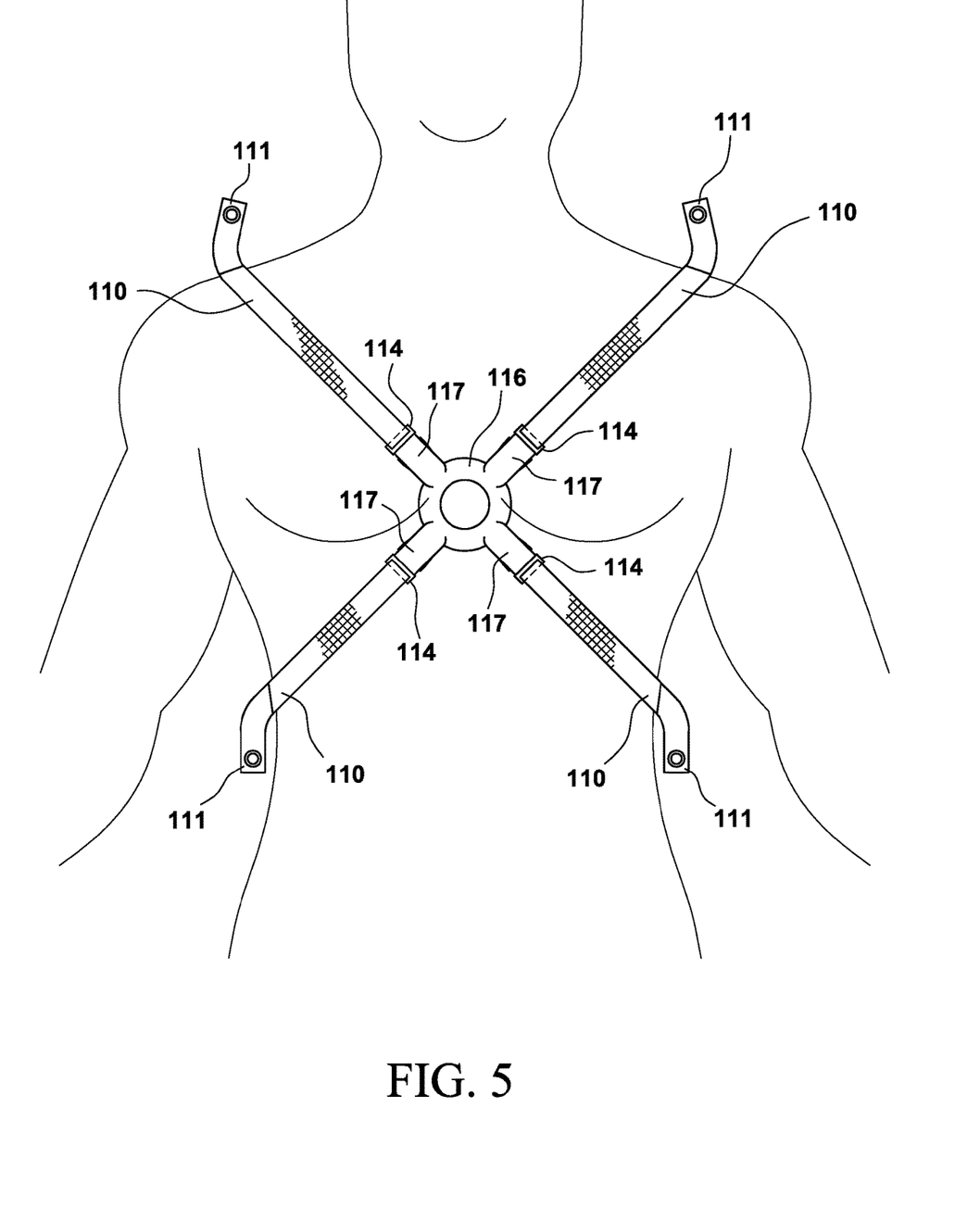
FIG. 5 is a front anterior perspective view of a person wearing the flexible support garment with embedded magnets according to the exemplary embodiment.

In FIG. 5, a front anterior perspective view of a person wearing the flexible support garment with embedded magnets according to the exemplary embodiment is shown. As shown in FIG. 5, two securing and rod locating straps 110 are draped over the patient's shoulders and two securing and rod locating straps 110 are wrapped around the patient's waist. The connector 114 at the end of each of the four securing and rod locating straps 110 to corresponding individual connectors 117 on a central connector 116.

The non-metallic rigid connection rod interfaces 111 on the patient's left shoulder and right hip are positioned as to generally align with each other. Similarly, the non-metallic rigid connection rod interfaces 111 on the patient's right shoulder and left hip are positioned to generally align with each other. The connection rod interface pairs are aligned in this manner such that lines drawn between each pair forms an X pattern that is generally centered on the patient's back.

While the flexible garment in this exemplary embodiment is shown as being comprised of interconnecting corner and expansion components, the flexible garment may be comprised solely of a single piece of fabric while clearly remaining within the scope of the present disclosure.

Figure 6:
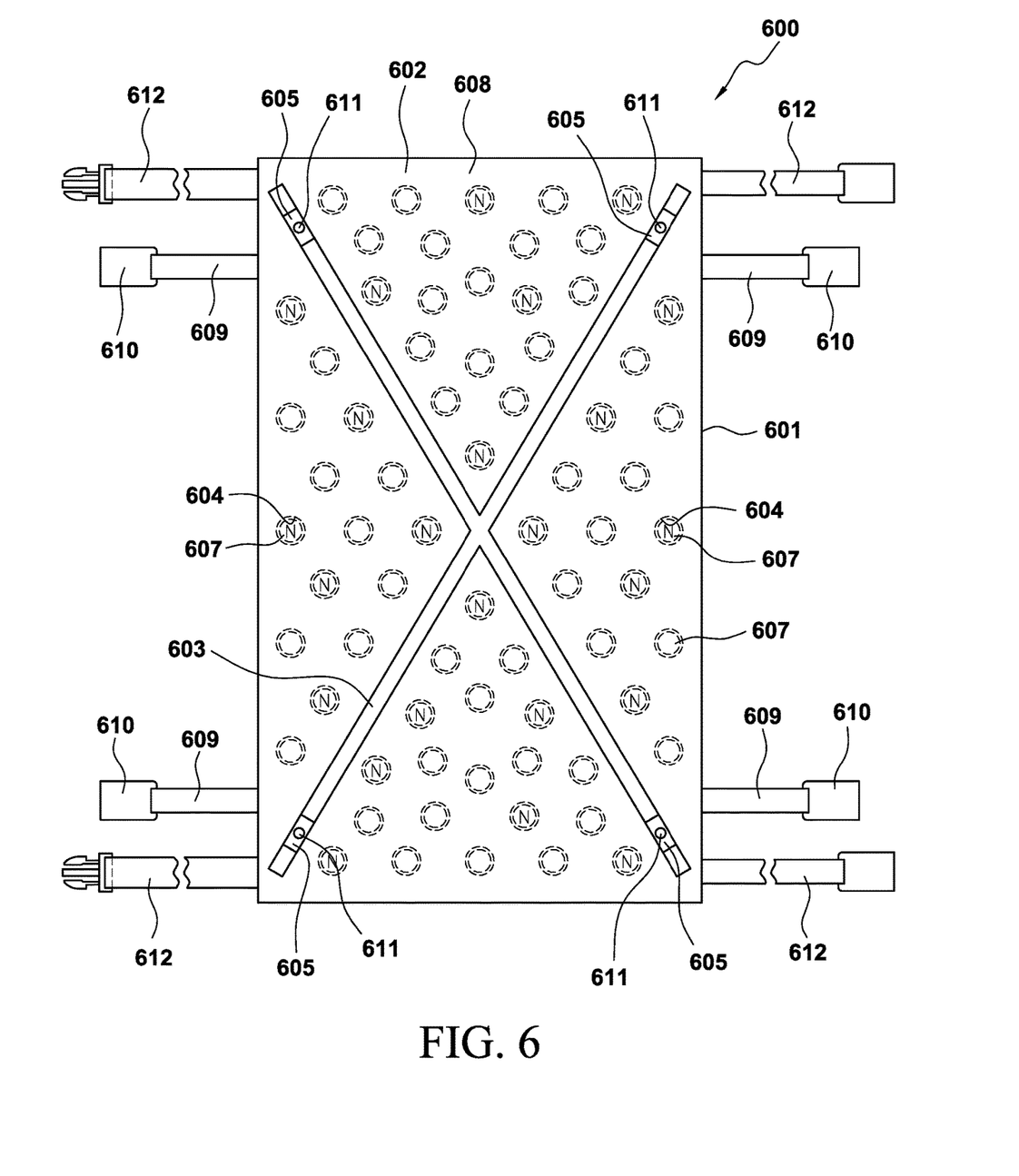
FIG. 6 is a rigid base component with embedded magnets according to an exemplary embodiment.

In FIG. 6 a rigid base component with embedded magnets according to an exemplary embodiment is shown. As shown in FIG. 6, the rigid base component 600 includes a rigid base member 601 made of a non-ferrous rigid core with an outer surface 602 covered by a flexible non-ferrous fabric. The size and shape of the rigid base member 601 may vary depending on the shape and size of the flexible support garment 100 with which it is interacting while remaining within the scope of the present invention.

The rigid base member 601 includes a pair of embedded channels 603 which cross each other within the outer surface 602, the embedded channels 603 generally forming an X within the outer surface 602. A pair of connection rod assemblies 605 is movably installed in each of the embedded channels 603. Each connection rod assembly 605 includes a rigid rod 611 made of a non-ferrous material extending vertically upward from the outer surface 602. Each of the four rigid rods 611 couples to a non-metallic rigid connection rod interface 111 on a flexible support garment 100. A non-metallic rigid connection rod interface 111 on a flexible support garment 100 may travel along the longitudinal length of the rigid rod 611 to which it is coupled. This coupling between a non-metallic rigid connection rod interface 111 and a rigid rod 611 provides for controlling the lateral and vertical movement of the elevated flexible support garment 100 relative to rigid base member 601. The connection rod assemblies 605 may travel the full length of the embedded channel 603 in which it is installed and may be secured in place at any position along that full longitudinal length.

The rigid base member 601 further includes a plurality of depressions 604 evenly distributed across the outer surface 602. The depressions 604 are sized and shaped to hold one or more permanent magnets 607. As with the flexible support garment 100, these permanent magnets 607 are all similarly oriented such that the magnetic north pole N of each magnet 607 emanates upward from the outer surface 602. The ability of each depression 604 to hold one or more permanent magnet 607 allows for the creation of variations in the strength of the magnetic field emanating upward from the outer surface 602. The distribution, size, and spacing of the permanent magnets 607 across the outer surface 602 may be customized to satisfy a patient's specific needs.

A removable cover 608 made of a flexible non-ferrous material is positioned over and against the outer surface 602, the cover 608 ensuring the retention of the permanent magnets 607 within the depressions 604 while allowing easy access to each of the depressions 604. The magnetic field emanating from the outer surface 602 will interact with a similar magnetic field originating from the flexible support garment 100, this interaction providing the required levitation of the flexible support garment 100.

While the depressions 604 are shown evenly distribute across the outer surface 602, different distributions of the depressions across the outer surface 606 are envisioned and are within the scope of the present invention.

As with the flexible support garment 100, while the disclosed embodiments are not limited to any particular type of permanent magnets, an N52 grade neodymium magnet have been found to be minimally suitable and advantageous to use.

The rigid base component 600 further includes flexible connecting straps 609 attached to opposite edges near each corner of the rigid base member 601. The flexible connecting straps 609 each include a connector 610 that connect to a connector 113 on the flexible connection 112 attached to the flexible support garment 100. The connectors 610 provide for adjusting the length of each of the flexible connecting straps 609. The connecting straps are generally positioned as to have one pair above the intersection point of the embedded channels 603 and the other pair below that same intersection point. Moreover, the specific position of the connecting straps 609 along the edges of the base member 601 may be adjustable.

A plurality of securing straps 612 are also permanently attached along edge of the of the rigid base member 601. These securing straps 612 interact in any manner know to one of reasonable skill in art to help secure the rigid base member 601 to an object on which it rests and that functions as an anchor such as a bed.

Figure 7:
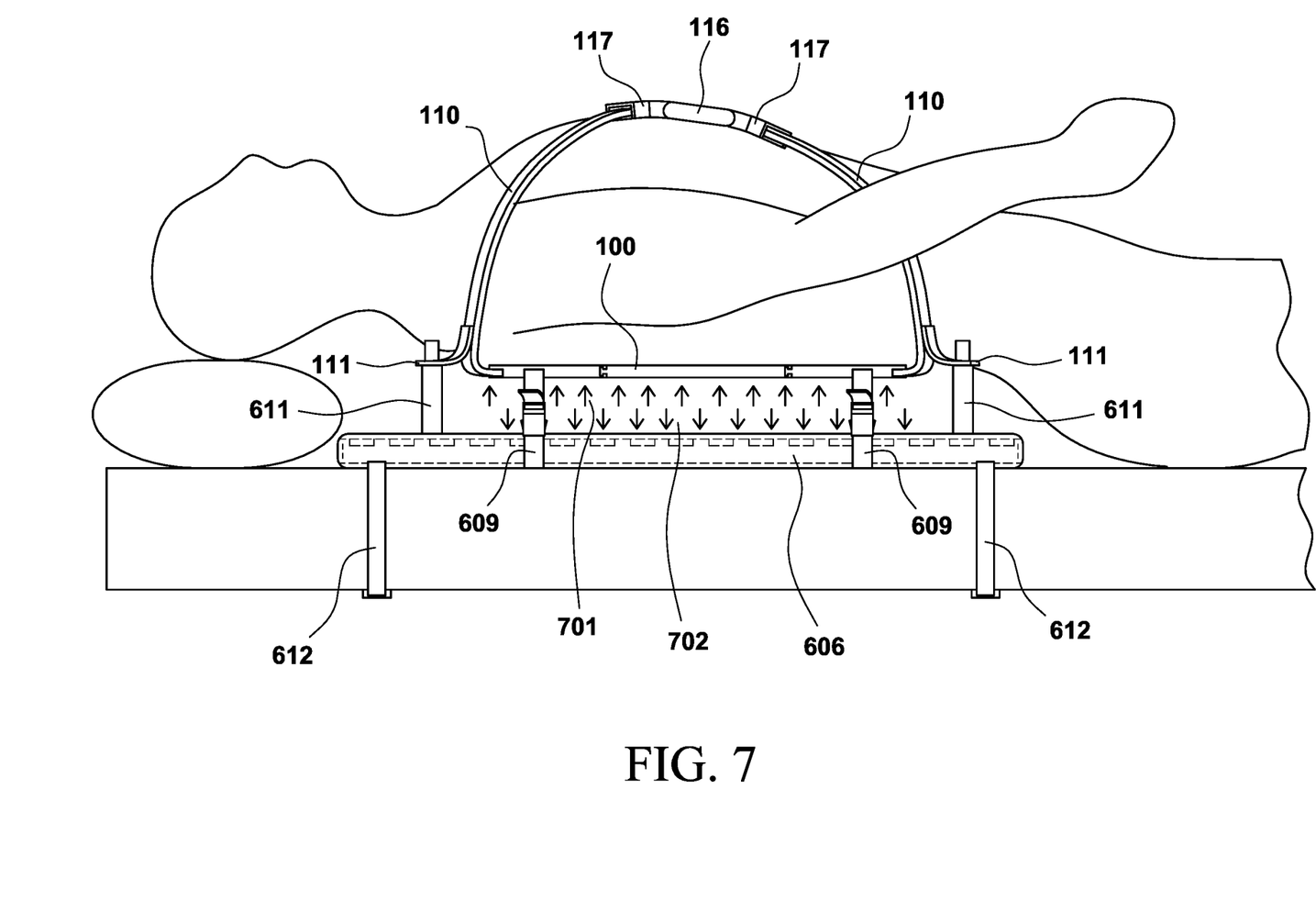
FIG. 7 is a flexible support garment interacting with the rigid base component according to an exemplary embodiment.

In FIG. 7, the flexible support garment interacting with the rigid base component according to an exemplary embodiment is shown. As shown in FIG. 7, the magnetic field 701 emanating from the flexible support garment 100 and the magnetic field 702 emanating from the rigid base component 600 repel each thereby create an upward force that elevates the flexible support garment 100 above the rigid base component 600. While the flexible support garment 100 is secured to a patient, the individual magnetic fields 701 and 702 will interact with each other in a manner that helps elevated that portion of the patient's back containing the wound 115 (FIG. 4).

While the flexible support garment 100 is suspended over the rigid base component 600, each rigid rod 611 extending from the embedded channels 603 is coupled to a corresponding non-metallic rigid connection rod interface 111 on the flexible support garment 100. Since the rigid rods 611 are themselves rigid and are secured within the embedded channels 603 via the connection rod assemblies 605, the lateral movement of the elevated portion of the patient relative to the rigid base component 600 is minimized. Moreover, the vertical movement of the elevated portion of the patient is limited to the longitudinal length of the rigid rod 611.

Figure 8A:
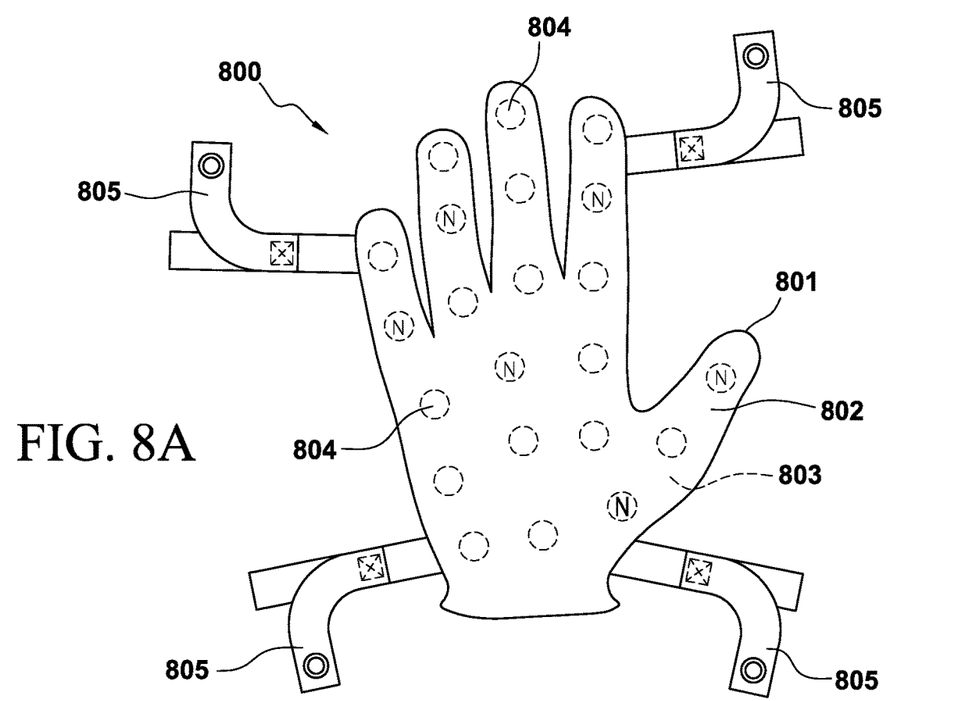
FIGS. 8A and 8B are an alternate embodiment of the flexible support garment with embedded magnets according to an exemplary embodiment.
Figure 8B:
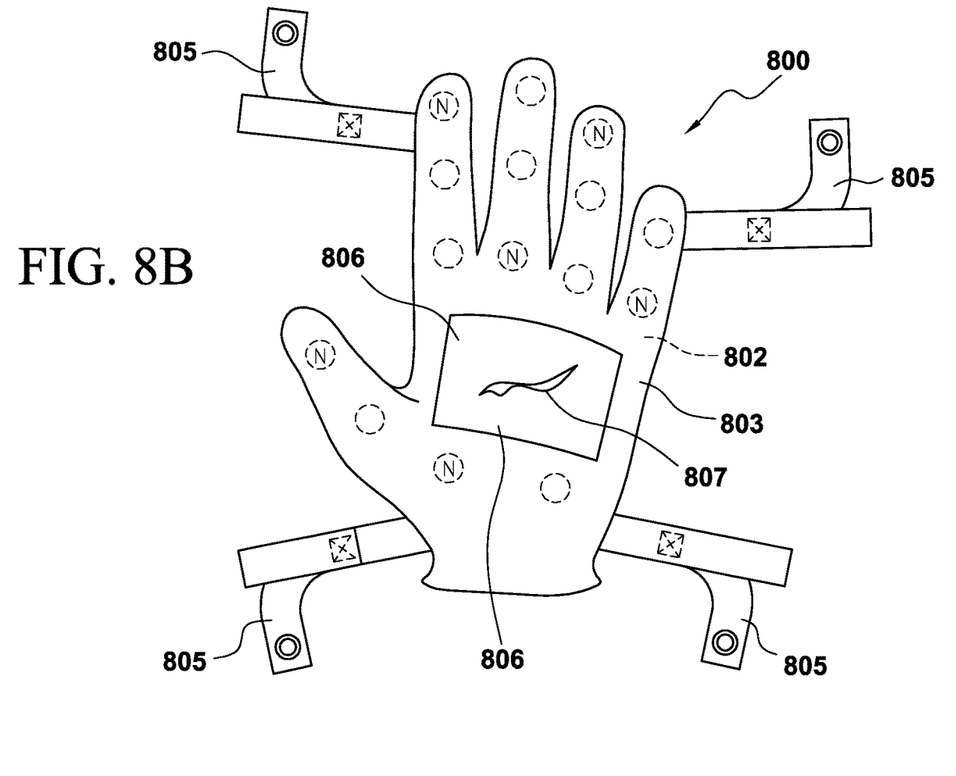

In FIGS. 8A and 8B, an alternate embodiment of the flexible support garment with embedded magnets according to an exemplary embodiment is shown. As shown in FIG. 8A, in this exemplary embodiment, the flexible support garment 800 is comprised of flexible body member 801 with a glove like shape that covers at least an outer portion 802 and a palm portion 803 of a patient's hand. A plurality of permanent magnets 804 are embedded throughout the outer portion 802 of the body member 801. The permanent magnets 804 are evenly spaced apart and are oriented such that each magnet's magnetic north pole N emanates outward from the outer palm portion 802. A connection rod interface 805 is attached to the body member 801 at four locations along its perimeter. The four connection rod interfaces 805 are positioned to effectively interface with rigid rods installed within the embedded channels of a rigid base components, as previously described.

As shown in FIG. 8B, the palm portion 803 includes an opening 806 which provide for leaving exposed a wound 807 on the patient's hand. The location of the opening 806 may vary dependent on the location of the wound.

Figure 9:
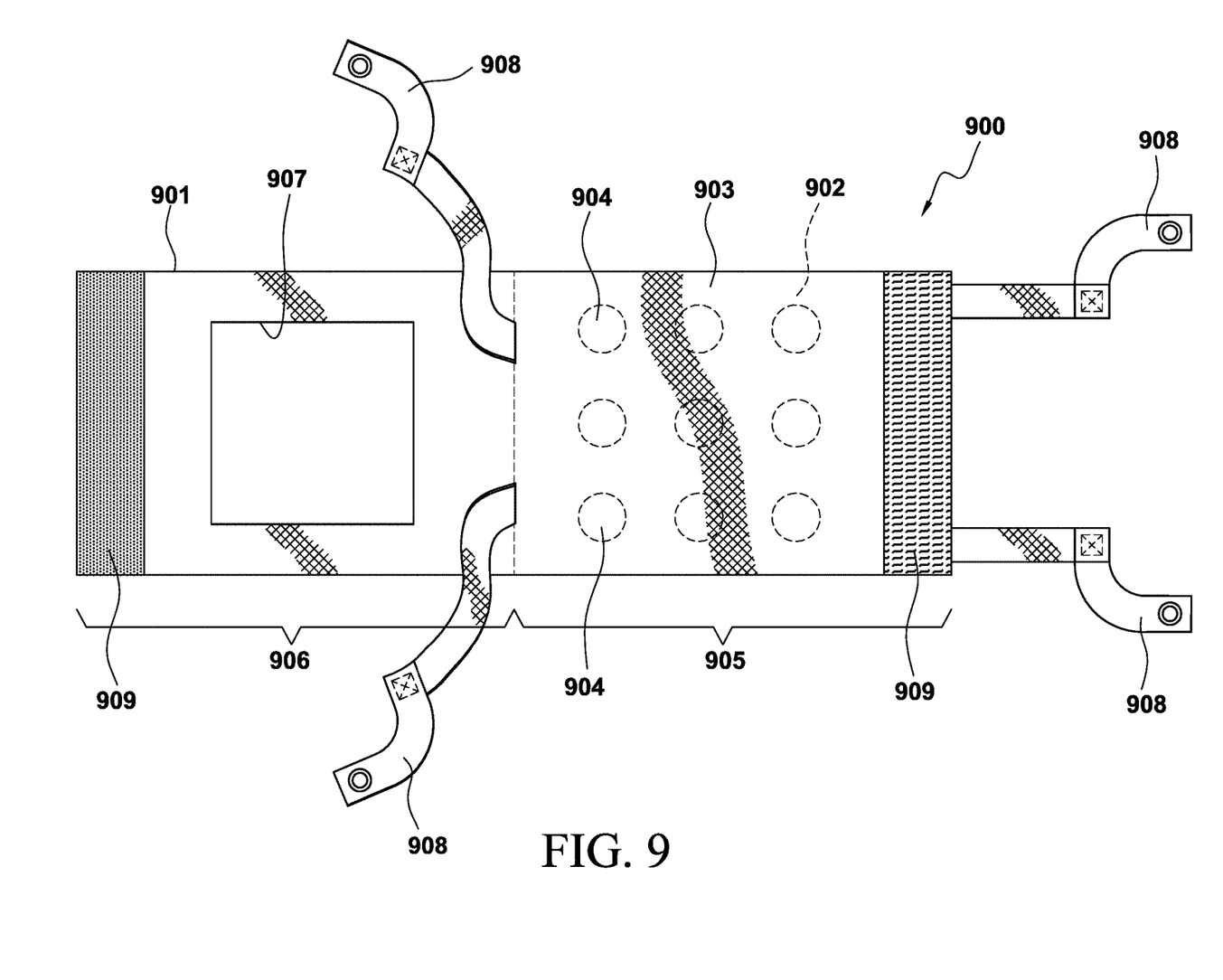
FIG. 9 is another alternate embodiment of the flexible support garment with embedded magnets according to an exemplary embodiment.

In FIG. 9, another alternate embodiment of the flexible support garment with embedded magnets according to an exemplary embodiment is shown. As shown in FIG. 9, in this exemplary embodiment, the flexible support garment 900 is comprised of flexible body member 901 having a rectangular like shape designed to be secured at any point along a patient's limb, the body member 901 having a inner surface 902 that comes into contact with patient's limb and an outer surface 903 facing outward from the patient's limb. A plurality of permanent magnets 904 are embedded throughout a first portion 905 the body member 901. The permanent magnets 904 are evenly spaced apart and are oriented such that each magnet's magnetic north pole N emanates outward from the outer surface 903. A second portion 906 of the body member 901 includes and open portion 907 providing for leaving exposed a patient's wound. A connection rod interface 908 is attached at four locations along the perimeter of the first portion 905. The four connection rod interfaces 908 are positioned to effectively interface with the rigid rods installed within the embedded channels of a rigid base components, as previously described. A Velcro strip 909 at each longitudinal end of the body member 901 are used to secure the flexible support garment 900 around a patient's limb while leaving the patient's wound exposed.

What is claimed:

1. A medical surgical wound support device comprising:
    a flexible support garment designed to be worn by a patient;
    the flexible support garment has an inner surface that comes in direct contact with the patient and an outer surface facing outward from the patient;
    a plurality of permanent magnets embedded within the flexible support garment, each embedded magnet oriented such that its north magnetic pole emanates outward from the outer surface;
    a rigid base member having an outer surface facing upward from a support on which the rigid base member rests and including a pair of embedded channels that cross to form an X within the outer surface of the rigid base member;
    a plurality of permanent magnets embedded within the outer surface of the rigid base member, each of which is oriented such that the north magnetic pole emanates outward from the outer surface of the rigid base member;

a repelling magnetic force originating from the outer surface of the flexible support garment and the outer surface of the rigid base member such that a portion of the patient wearing the flexible support garment is elevated a controllable distance above the rigid base member;

a pair of telescopic rods made of a non-ferrous material positioned within each of the embedded channels and extending upward from the outer surface of the rigid base member, the telescopic rods able to be secured at any position along a longitudinal length of the embedded channel in which it is positioned; and four connection rod interfaces attached to the flexible support garment, each of the four connection rod interfaces coupling to one of the telescopic rods while the flexible support garment is elevated a distance above the rigid base member.

2. The medical surgical wound support device of claim 1 wherein the flexible support garment includes an opening of sufficient size to leave a patient's wound exposed while wearing the flexible support garment.

3. The medical surgical wound support device of claim 1 further including a plurality of flexible connection straps that connect the flexible support garment to the rigid base member;

the flexible connection straps are attached directly to perimeters of the flexible support garment and of the rigid base member so as to limit the lateral and vertical movement of the elevated patient relative to the rigid base member and allowing for maximum levitation.

4. The medical surgical wound support device of claim 1 wherein the flexible support garment is comprised of four corner components and a plurality of size expansion components, the corner components having a general L shape that form the corners of the flexible support garment, and the size expansion components having a rectangular shape that form the areas in-between the individual corner components; and wherein the corner components and the size expansion component are arranged and interconnected such that the flexible support garment is shaped and sized to be secured onto the patient's back.

5. The medical surgical wound support device of claim 1 wherein the flexible support garment is glove shaped such that the flexible support garment is shaped and sized to be secured onto the patient's hand.

6. The medical surgical wound support device of claim 1 wherein the flexible support garment is rectangular shaped such that the flexible support garment is sized and shaped to be secured onto the patient's limb.

7. The medical surgical wound support device of claim 1 wherein the outer surface of the rigid base member includes a plurality of depressions within which the plurality of magnets are contained within; and the depressions allowing for the insertion and staking of a plurality of magnets in each individual depression and thereby customize the strength of the magnetic field emanating from each of the depressions.

* * * * *